US006936443B2

(12) United States Patent
Cohenford et al.

(10) Patent No.: US 6,936,443 B2
(45) Date of Patent: Aug. 30, 2005

(54) DETECTION AND TYPING OF HUMAN PAPILLOMAVIRUS USING PNA PROBES

(75) Inventors: Menashi A. Cohenford, West Warwick, RI (US); Brian Lentrichia, Acton, MA (US)

(73) Assignee: Cytyc Corporation, Marlborough, MA (US)

(*) Notice: Subject to any disclaimer, the term of this patent is extended or adjusted under 35 U.S.C. 154(b) by 293 days.

(21) Appl. No.: 10/286,387

(22) Filed: Nov. 1, 2002

(65) Prior Publication Data

US 2003/0143529 A1 Jul. 31, 2003

Related U.S. Application Data

(63) Continuation-in-part of application No. 09/825,482, filed on Apr. 3, 2001.
(60) Provisional application No. 60/194,304, filed on Apr. 3, 2000, and provisional application No. 60/225,524, filed on Aug. 15, 2000.

(51) Int. Cl.[7] .................. C12P 19/34; C07H 21/02; C07H 21/04
(52) U.S. Cl. .................. 435/91.2; 536/23.1; 536/24.3
(58) Field of Search .................. 435/91.2; 536/23.1, 536/24.3

(56) References Cited

U.S. PATENT DOCUMENTS

| | | |
|---|---|---|
| 4,849,332 A | 7/1989 | Lorincz |
| 4,908,306 A | 3/1990 | Lorincz |
| 4,983,728 A | 1/1991 | Herzog et al. |
| 5,143,627 A | 9/1992 | Lapidus et al. |
| 5,182,377 A | 1/1993 | Manos et al. |
| 5,256,571 A | 10/1993 | Hurley et al. |
| 5,283,171 A | 2/1994 | Manos et al. |
| 5,364,758 A | 11/1994 | Meijer et al. |
| 5,411,857 A | 5/1995 | Beaudenon et al. |
| 5,447,839 A | 9/1995 | Manos et al. |
| 5,484,699 A | 1/1996 | Bouma et al. |
| 5,527,898 A | 6/1996 | Bauer et al. |
| 5,539,082 A | 7/1996 | Nielsen et al. |
| 5,543,294 A | 8/1996 | Silverstein et al. |
| 5,580,970 A | 12/1996 | Hendricks et al. |
| 5,629,178 A | 5/1997 | Demers |
| 5,639,871 A | 6/1997 | Bauer et al. |
| 5,643,715 A | 7/1997 | Lancaster |
| 5,648,459 A | 7/1997 | Cole et al. |
| 5,656,461 A | 8/1997 | Demers |
| 5,679,509 A | 10/1997 | Wheeler et al. |
| 5,705,627 A | 1/1998 | Manos et al. |
| 5,712,092 A | 1/1998 | Orth et al. |
| 5,719,028 A | 2/1998 | Dahlberg et al. |
| 5,731,416 A | 3/1998 | Garner |
| 5,750,334 A | 5/1998 | Cerutti et al. |
| 5,783,412 A | 7/1998 | Morris et al. |
| 5,837,466 A | 11/1998 | Lane et al. |
| 5,846,729 A | 12/1998 | Wu et al. |
| 5,854,033 A | 12/1998 | Lizardi |
| 5,874,213 A | 2/1999 | Cummins et al. |
| 5,876,922 A | 3/1999 | Orth et al. |
| 5,888,724 A | 3/1999 | Silverstein et al. |
| 5,888,733 A | 3/1999 | Hyldig-Nielsen et al. |
| 5,891,625 A | 4/1999 | Buchardt et al. |
| 5,942,391 A | 8/1999 | Zhang et al. |
| 5,958,674 A | 9/1999 | Beaudenon et al. |
| 5,958,738 A | 9/1999 | Lindemann et al. |
| 5,981,173 A | 11/1999 | Orth et al. |
| 5,985,563 A | 11/1999 | Hyldig-Nielsen et al. |
| 6,020,124 A | 2/2000 | Sorenson |
| 6,037,130 A | 3/2000 | Tyagi et al. |
| 6,110,676 A | 8/2000 | Coull et al. |
| 6,218,104 B1 | 4/2001 | Morris et al. |
| 6,509,149 B2 | 1/2003 | Roberts et al. |

FOREIGN PATENT DOCUMENTS

| | | |
|---|---|---|
| WO | WO 92/20702 | 11/1992 |
| WO | WO 95/13399 | 5/1995 |
| WO | WO 97/39008 | 10/1997 |

OTHER PUBLICATIONS

"Detection of E6 Gene Region DNA of High–Risk Human Papillomavirus Types Using E6 Gene Region Primers" *Biosearch International*, Aug. 2000, pp. 1–22.
Behn M. et al., "Simple and Reliable Factor V Genotyping by PNA–Mediated PCR Clamping" *Thromb Haemost.* vol. 79, 1998, pp. 773–777.
Cochet O. et al., "Selective PCR Amplification of Functional Immunoglobulin Light Chain from Hybridoma Containing the Aberrant MOPC 21–Derived Vλ by PNA–Mediated PCR Clamping" *Biotechniques.* vol. 26, No. 5, 1999, 818–822.
Demers D. B. et al., "Enhanced PCR Amplification of VNTR Locus DIS80 Using Peptide Nucleic Acid (PNA)" *Nucleic Acids Research.* vol. 23, No. 15, 1995, pp 3050–3055.
Hansen M. H. et al., "Detection of PNA/DNA Hybrid Molecules by Antibody Fab Fragments Isolated from a Phage Display Library" *Journal of Immunological Methods.* vol. 203, No. 2, 1997, pp. 199–207.
Kyger E. M. et al., "Detection of the Hereditary Hemochromatosis Gene Mutation by Real–Time Fluorescence Polymerase Chain Reaction and Peptide Nucleic Acid Clamping" *Analytical Biochemistry.* vol. 260, No. 2, 1998, pp 142–148.
Mrozikiewicz O.M. et al., "Peptide Nucleic Acid–Mediated Polymerase Chain Reaction Clamping Allows Allelic Allocation of CYPIA1 Mutations" *Analytical Biochemistry.* vol. 250, No. 2, 1997, pp. 256–257.

(Continued)

*Primary Examiner*—Jeffrey Fredman
*Assistant Examiner*—Teresa Strzelecka
(74) *Attorney, Agent, or Firm*—Theodore Allen; Mark J. Casey

(57) ABSTRACT

The invention provides materials and methods for detection and typing of HPV infection using PNA probes. More specifically, methods are provided for detecting high-risk types of HPV infection with minimal numbers of PNA probes or using PNA probes to selectively amplify only high-risk types of HPV. Novel primer sequences are also provided.

15 Claims, 4 Drawing Sheets

OTHER PUBLICATIONS

Orum H. et al., "Single Base Pair Mutation Analysis by PNA Direct PCT Clamping" *Nucleic Acids Research*. Vo 21, No. 23, 1993, pp 5332–5336.

Seeger et al. "PNA–Mediated Purification of PCR Amplifiable Human Genome DNA from Whole Blood" *Biotechniques*. vol. 23, No. 3, 1997, pp. 312–317.

Uhlmann F., "Peptide Nucleic Acids (PNA) and PNA–DNA Chimerase From High Binding Affinity Towards Biological Function" *Biol. Chemistry*, 1998, 379 (8–9) pp. 1044–1052.

von Wintzingerods F. et al., "Peptide Nucleic Acid–Mediated PCR Clamping as a Useful Supplement in the Determination of Microbial Diversity" *Applied and Environmental Microbiology*, vol. 66, No. 2, Feb. 2000, pp. 549–557.

Zhong S et al., "Detection of Apoliporotein B mRNA Editing by Peptide Nucleic Acid Mediated PCR Clamping" *Biochemical and Biophysical Research Communication*, vol. 259, No. 2, 1999, pp. 311–313.

Lane 1: DNA Ladder

Lane 2: HPV DNA Strain 11, in absence of PNA

Lane 3: HPV DNA Strain 16, in absence of PNA

Lane 4: HPV DNA Strain 18, in absence of PNA

Lane 5: HPV DNA Strain 11 in presence of PNA I

Lane 6: HPV DNA Strain 16 in presence of PNA I

Lane 7: HPV DNA Strain 18 win presence of PNA I

Lane 8: HPV DNA Strain 11 in presence of PNA II

Lane 9: HPV DNA Strain 16 in presence of PNA II

Lane 10: HPV DNA Strain 18 in presence of PNA II

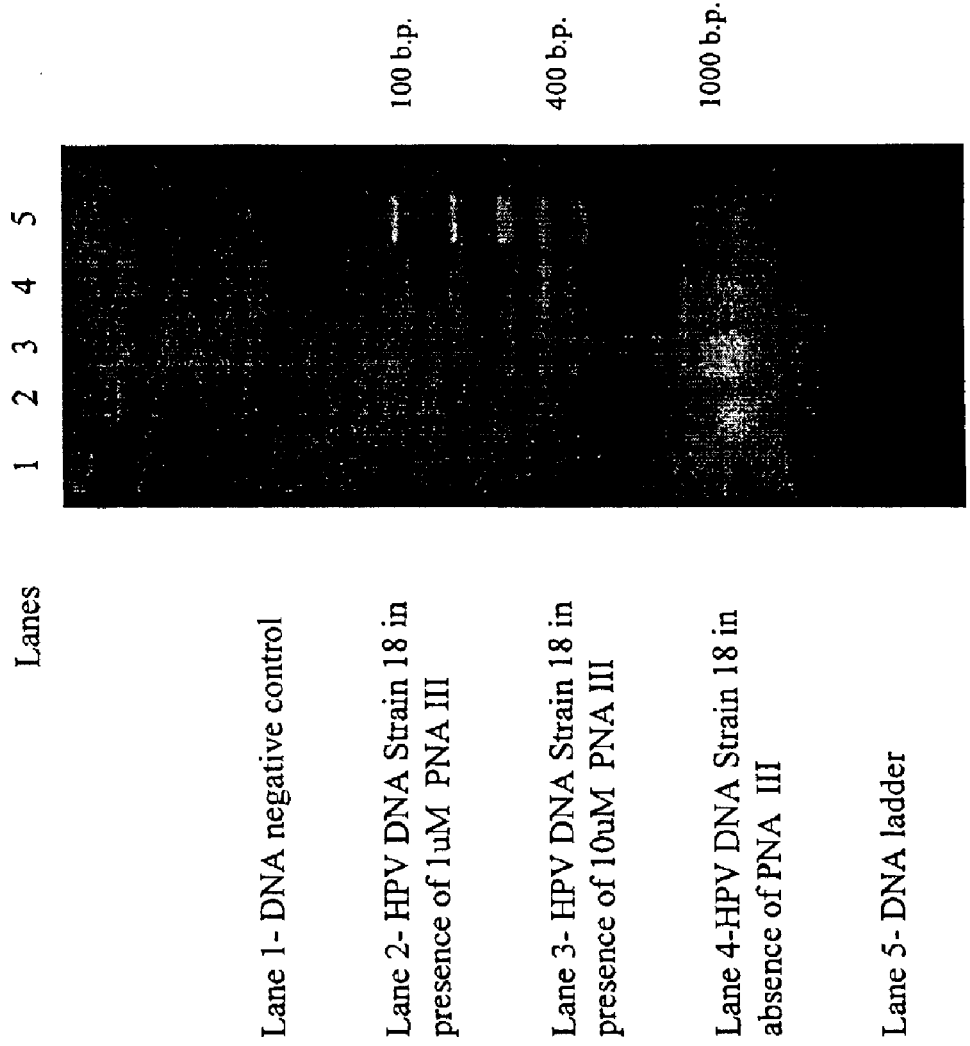

SEQUENCE LISTING

<160> NUMBER OF SEQ ID NOS: 31

<210> SEQ ID NO 1
<211> LENGTH: 15
<212> TYPE: DNA
<213> ORGANISM: Artificial
<220> FEATURE:
<223> OTHER INFORMATION: PNA probe

<400> SEQUENCE: 1
actgttgttg atact                                                    15

<210> SEQ ID NO 2
<211> LENGTH: 14
<212> TYPE: DNA
<213> ORGANISM: Artificial
<220> FEATURE:
<223> OTHER INFORMATION: PNA probe

<400> SEQUENCE: 2
agataccact ccca                                                     14

<210> SEQ ID NO 3
<211> LENGTH: 14
<212> TYPE: DNA
<213> ORGANISM: Artificial
<220> FEATURE:
<223> OTHER INFORMATION: PNA probe

<400> SEQUENCE: 3
gataccactc gcag                                                     14

<210> SEQ ID NO 4
<211> LENGTH: 14
<212> TYPE: DNA
<213> ORGANISM: Artificial
<220> FEATURE:
<223> OTHER INFORMATION: PNA probe

<400> SEQUENCE: 4
ccttacacca ccgc                                                     14

<210> SEQ ID NO 5
<211> LENGTH: 14
<212> TYPE: DNA
<213> ORGANISM: Artificial
<220> FEATURE:

```
<223> OTHER INFORMATION: PNA probe

<400> SEQUENCE: 5
gacactaccc gcag                                                      14

<210> SEQ ID NO 6
<211> LENGTH: 20
<212> TYPE: DNA
<213> ORGANISM: Artificial
<220> FEATURE:
<223> OTHER INFORMATION: Consensus primer used to amplify cervical DNA
      specimen

<400> SEQUENCE: 6
cgtccmarrg gawactgatc                                                20

<210> SEQ ID NO 7
<211> LENGTH: 20
<212> TYPE: DNA
<213> ORGANISM: Artificial
<220> FEATURE:
<223> OTHER INFORMATION: Consensus primer used to amplify cervical DNA
      specimen

<400> SEQUENCE: 7
gcmcagggwc ataayaatgg                                                20

<210> SEQ ID NO 8
<211> LENGTH: 20
<212> TYPE: DNA
<213> ORGANISM: Artificial
<220> FEATURE:
<223> OTHER INFORMATION: Forward primer used to amplify region of E6 ORF
      of HPV

<400> SEQUENCE: 8
tgtcaaaaac cgttgtgtcc                                                20

<210> SEQ ID NO 9
<211> LENGTH: 23
<212> TYPE: DNA
<213> ORGANISM: Artificial
<220> FEATURE:
<223> OTHER INFORMATION: Forward primer used to amplify region of E6 ORF
      of HPV

<400> SEQUENCE: 9
tgtcaaaaac cgttgtgtcc aac                                            23

<210> SEQ ID NO 10
<211> LENGTH: 23
<212> TYPE: DNA
<213> ORGANISM: Artificial
<220> FEATURE:
<223> OTHER INFORMATION: Forward primer used to amplify region of E6 ORF
      of HPV

<400> SEQUENCE: 10
tgtcaaaaac cgttgtgtcc agc                                            23

<210> SEQ ID NO 11
<211> LENGTH: 20
<212> TYPE: DNA
<213> ORGANISM: Artificial
<220> FEATURE:
<223> OTHER INFORMATION: Forward primer used to amplify region of E6 ORF
      of HPV
```

<400> SEQUENCE: 11
tgccagaaac cattgaaccc                                         20

<210> SEQ ID NO 12
<211> LENGTH: 20
<212> TYPE: DNA
<213> ORGANISM: Artificial
<220> FEATURE:
<223> OTHER INFORMATION: Forward primer used to amplify region of E6 ORF
      of HPV

<400> SEQUENCE: 12
tgtcaaagac cactcgtgcc                                         20

<210> SEQ ID NO 13
<211> LENGTH: 23
<212> TYPE: DNA
<213> ORGANISM: Artificial
<220> FEATURE:
<223> OTHER INFORMATION: Forward primer used to amplify region of E6 ORF
      of HPV

<400> SEQUENCE: 13
tgtcaaaaac cgttgtgtcc tga                                     23

<210> SEQ ID NO 14
<211> LENGTH: 22
<212> TYPE: DNA
<213> ORGANISM: Artificial
<220> FEATURE:
<223> OTHER INFORMATION: Forward primer used to amplify region of E6 ORF
      of HPV

<400> SEQUENCE: 14
tatgtgattt gttaattagg tg                                      22

<210> SEQ ID NO 15
<211> LENGTH: 20
<212> TYPE: DNA
<213> ORGANISM: Artificial
<220> FEATURE:
<223> OTHER INFORMATION: Forward primer used to amplify region of E6 ORF
      of HPV

<400> SEQUENCE: 15
tgccaaaaac cactgtgtcc                                         20

<210> SEQ ID NO 16
<211> LENGTH: 20
<212> TYPE: DNA
<213> ORGANISM: Artificial
<220> FEATURE:
<223> OTHER INFORMATION: Reverse primer used to amplify region of E6 ORF
      of HPV

<400> SEQUENCE: 16
gagctgtcgc ttaattgctc                                         20

<210> SEQ ID NO 17
<211> LENGTH: 20
<212> TYPE: DNA
<213> ORGANISM: Artificial
<220> FEATURE:
<223> OTHER INFORMATION: Reverse primer used to amplify region of E6 ORF
      of HPV

```
<400> SEQUENCE: 17
tctgagtctc gtaattgctc                                          20

<210> SEQ ID NO 18
<211> LENGTH: 20
<212> TYPE: DNA
<213> ORGANISM: Artificial
<220> FEATURE:
<223> OTHER INFORMATION: Reverse primer used to amplify region of E6 ORF
      of HPV

<400> SEQUENCE: 18
tctgactcgc tttattgctc                                          20

<210> SEQ ID NO 19
<211> LENGTH: 20
<212> TYPE: DNA
<213> ORGANISM: Artificial
<220> FEATURE:
<223> OTHER INFORMATION: Reverse primer used to amplify region of E6 ORF
      of HPV

<400> SEQUENCE: 19
tctgtgctgt caacttactc                                          20

<210> SEQ ID NO 20
<211> LENGTH: 21
<212> TYPE: DNA
<213> ORGANISM: Artificial
<220> FEATURE:
<223> OTHER INFORMATION: Reverse primer used to amplify region of E6 ORF
      of HPV

<400> SEQUENCE: 20
ctgagctgtc taattgctcg t                                        21

<210> SEQ ID NO 21
<211> LENGTH: 21
<212> TYPE: DNA
<213> ORGANISM: Artificial
<220> FEATURE:
<223> OTHER INFORMATION: Reverse primer used to amplify region of E6 ORF
      of HPV

<400> SEQUENCE: 21
ctctgtgtcg ctaaattgct c                                        21

<210> SEQ ID NO 22
<211> LENGTH: 39
<212> TYPE: DNA
<213> ORGANISM: Artificial
<220> FEATURE:
<223> OTHER INFORMATION: Beacon technology PNA-DNA chimeric probe

<400> SEQUENCE: 22
ggcacatcat caagaacccg tagagaaacc cagcgtgcc                      39

<210> SEQ ID NO 23
<211> LENGTH: 15
<212> TYPE: DNA
<213> ORGANISM: Artificial
<220> FEATURE:
<223> OTHER INFORMATION: PNA probe

<400> SEQUENCE: 23
agataccaca cgcag                                               15
```

<210> SEQ ID NO 24
<211> LENGTH: 17
<212> TYPE: DNA
<213> ORGANISM: Artificial
<220> FEATURE:
<223> OTHER INFORMATION: PNA probe

<400> SEQUENCE: 24
tagataccac acgcagt                                                    17

<210> SEQ ID NO 25
<211> LENGTH: 15
<212> TYPE: DNA
<213> ORGANISM: Artificial
<220> FEATURE:
<223> OTHER INFORMATION: PNA probe

<400> SEQUENCE: 25
agataccact cccag                                                      15

<210> SEQ ID NO 26
<211> LENGTH: 22
<212> TYPE: DNA
<213> ORGANISM: Artificial
<220> FEATURE:
<223> OTHER INFORMATION: Modified consensus primer for amplifying
      multiple HPV strains

<400> SEQUENCE: 26
tgaggaagat accacacgca gt                                              22

<210> SEQ ID NO 27
<211> LENGTH: 12
<212> TYPE: DNA
<213> ORGANISM: Artificial
<220> FEATURE:
<223> OTHER INFORMATION: PNA probe

<400> SEQUENCE: 27
gtgaagtaga aa                                                         12

<210> SEQ ID NO 28
<211> LENGTH: 12
<212> TYPE: DNA
<213> ORGANISM: Artificial
<220> FEATURE:
<223> OTHER INFORMATION: PNA probe

<400> SEQUENCE: 28
gtgtgaagta ga                                                         12

<210> SEQ ID NO 29
<211> LENGTH: 13
<212> TYPE: DNA
<213> ORGANISM: Artificial
<220> FEATURE:
<223> OTHER INFORMATION: PNA probe

<400> SEQUENCE: 29
ctgtgtgaag tag                                                        13

<210> SEQ ID NO 30
<211> LENGTH: 12
<212> TYPE: DNA
<213> ORGANISM: Artificial

-continued

```
<220> FEATURE:
<223> OTHER INFORMATION: PNA probe

<400> SEQUENCE: 30
gctgtgtgaa gt                                                            12

<210> SEQ ID NO 31
<211> LENGTH: 13
<212> TYPE: DNA
<213> ORGANISM: Artificial
<220> FEATURE:
<223> OTHER INFORMATION: PNA probe

<400> SEQUENCE: 31
cgttgtgtga aat                                                           13
```

DETECTION AND TYPING OF HUMAN PAPILLOMAVIRUS USING PNA PROBES

CROSS-REFERENCE TO RELATED APPLICATIONS

This application is a continuation-in-part of U.S. patent application Ser. No. 09/825,482, filed Apr. 3, 2001, which claims the benefit of U.S. provisional applications Nos. 60/194,304, filed Apr. 3, 2000, and 60/225,524, filed Aug. 15, 2000.

GOVERNMENT RIGHTS

Work described herein was supported by SBIR Grant No. 1R43CA80401-01, awarded by the National Cancer Institute. The Government has certain rights in the invention.

BACKGROUND OF THE INVENTION

Epidemiological studies have long implicated the human papillomavirus (HPV) as a major cause of cervical neoplasia and cancer. Nonetheless, it has been only within the last decade that a vast body of evidence has been generated to support a causal role of HPV in the etiology of cervical neoplasia and cancer. More than 100 types of HPV have been identified. However, not all HPV types are implicated in cervical cancer. Several types have been associated with a high risk for cervical disease, including types 16, 18, 31, 33, 35, 39, 45, 51, 52, 53, 56, 58, 59, 66, 68, and 70. The detection of these high-risk types of HPV is important in the accurate and timely diagnosis of HPV-related diseases.

Consequently, a variety of methods for detecting high-risk types of HPV have been devised. Many of those rely on the detection of unique sequences in the HPV genome. For example, DNA or RNA probes complementary to a portion of the genes of a particular high risk HPV strain have been reported in the art, e.g., in U.S. Pat. No. 4,849,332 to Lorincz, incorporated herein by reference, as useful in screening for the presence of a particular strain of high-risk HPV in patient samples. U.S. Pat. No. 5,705,627 to Manos et al., incorporated herein by reference, reports use of polymerase chain reaction (PCR) to amplify and detect HPV DNA using degenerate or mixed consensus primers, followed by typing using a mixture of genotype-specific DNA probes. Other examples of using consensus primers can be found in U.S. Pat. No. 5,364,758 to Meijer et al., and Kleter, B. et al., *Am. J. of Pathology*, vol. 153, No. 6, 1731–39 (1998). These references are also incorporated herein by reference to the extent applicable.

PCR amplification provides a more sensitive method of detecting HPV DNA, but because existing PCR consensus primers hybridize to both high-risk types of HPV and low-risk types, the need for subsequent typing still exists. Using a cocktail of probes specific for various high-risk genotypes, on the other hand, is costly, time-consuming and requires large quantities of reagents and sample DNA. Therefore, there exists the need for a more economical method of detecting all the high-risk HPV types that are of concern.

SUMMARY OF THE INVENTION

Methods of the invention comprise detecting and/or typing variants of a disease organism. In a preferred embodiment, methods are used to detect nucleic acids associated with HPV, which in turn provides a basis for medical diagnosis and treatment. Methods of the invention solve the problems in the art through two approaches: the first approach minimizes the amount of probes needed for screening for all the variants of concern, e.g., all the high-risk strains of a disease organism. The second approach limits the strains amplified by an amplification-based (e.g. PCR-based) detection method.

In one aspect of the invention, methods are provided for detecting the presence of specific HPV target nucleic acids in biological samples using peptide-nucleic acid (PNA) probes. Preferred methods comprise suspending sample cells in a solution; isolating one or more HPV target nucleic acids from the sample cells; contacting the target nucleic acids with at least one PNA probe that is substantially complementary to at least a portion of a nucleic acid, the detection of which is desired; and detecting hybridization between the PNA probe and a target nucleic acid. Preferably, the solution for suspending the sample cells contains an alcohol in an amount sufficient to fix sample cells without coagulation, an anti-clumping agent, and a buffer that maintains the solution at a pH within a range of about 4 to 7.

In one embodiment of the invention, the PNA probe is labeled with a detectable marker, such as a molecular beacon.

In a preferred embodiment, the presence of the target nucleic acid in the sample cells is diagnostic of HPV infection, and may be indicative of risks of cancer, such as risks associated with adenocarcinoma and squamous cell carcinoma of the cervix.

In another embodiment, the presence of the target nucleic acid sequence is indicative of the presence of a particular type of HPV. In more preferred embodiments, the target nucleic acid sequence is indicative of the presence of HPV strains selected from types 16, 18, 31, 33, 35, 39, 45, 51, 52, 56, 58, 59, 68 and 70.

In other preferred embodiments, methods of the invention further comprise capturing the target nucleic acid onto a solid support using PNA-DNA interaction.

Alternative embodiments of the invention include methods for detecting the presence of a target nucleic acid of a HPV in a sample, comprising: capturing candidate nucleic acids onto a solid support with at least one PNA probe that is substantially complementary to at least a portion of nucleic acids of one or more HPV types and then detecting hybridization between the PNA probe and a target nucleic acid. Other embodiments relate to methods for in situ detection of a target nucleic acid of a HPV in a sample by transferring suspended sample cells uniformly onto a surface; in situ hybridizing a target nucleic acid of a HPV contained in the cells with at least one PNA probe that is substantially complementary to portions of nucleic acids of one or more HPV types; and detecting hybridization between the PNA probe and a target nucleic acid.

Another aspect of the invention provides methods of detecting target nucleic acids comprising amplifying target nucleic acids, and blocking amplification of other nucleic acids, the detection of which is not desired. Such methods generally comprise providing a sample that may comprise nucleic acid from at least one selected strain of an organism and nucleic acid from at least one non-selected strain of the organism. Also provided are multiple primers substantially complementary to portions of nucleic acids from both selected strains and non-selected strains of the organism. The sample is exposed to at least one nucleic acid analog probe that is sufficiently complementary to a portion of the nucleic acid from at least one non-selected strain to block its full length amplification between the plurality of primers. The nucleic acid from at least one selected strain is amplified between the multiple primers and detection of such amplification product indicates the presence of at least one selected strain in the sample.

In a preferred embodiment, methods of the invention are used to bias a screening assay toward the diagnostically most-relevant strains or species of a disease organism. Accordingly, methods of the invention comprise exposing a biological sample to primer pairs for amplification of nucleic acids from selected strains or variants of a disease organism, and blocking amplification of nucleic acids from non-selected strains or variants of the organism. Preferably, the primer pairs used in methods of the invention universally amplify nucleic acid of all strains of the disease organism. Amplification is blocked only in non-selected strains or variants of the organism, such that only nucleic acids from selected strains or variants are amplified.

In a highly preferred embodiment, methods of the invention are used to selectively amplify high-risk strains of an infectious organism. In such methods, consensus primers for amplification of a preselected region of the infectious organism's genome are used. Alone, these primers are capable of amplifying nucleic acid from most or all of the strains or variants of the disease organism. However, in methods of the invention, amplification of non-selected strains or variants is blocked such that any amplicon produced is representative of only the unblocked strains or variants.

For example, methods of the invention are used to selectively detect high-risk strains of HPV. An amplification reaction is conducted in the presence of HPV consensus primers and one or more peptide nucleic acid blocking probes that hybridize only to a region at or between the primers in non-selected low-risk strains of HPV. The PNA blocking probes prevent amplification of nucleic acids from low-risk strains (i.e., full-length amplification between primers is prevented), while nucleic acids from high-risk strains to which the PNA blocking probes do not hybridize are amplified.

Methods of the invention are useful with any nucleic acid amplification method including those known in the art, such as polymerase chain reaction (PCR), ligase chain reaction (LCR), the rolling circle replication system, branched chain amplification, nucleic acid based sequence amplification (NASBA), Transcription-mediated Amplification (TMA), Cleavase Fragment Length Polymorphism (see, e.g. U.S. Pat. No. 5,719,028, incorporated herein by reference), and Isothermal and Chimeric Primer-initiated Amplification of Nucleic Acid (ICAN), and Ramification-extension Amplification Method (RAM) (see, e.g. U.S. Pat. No. 5,719,028, 5,942,391, incorporated herein by reference). Methods of the invention are useful to detect the presence in a biological sample of any disease organisms, including viruses and bacteria, such as herpes, hepatitis, gonorrhea, streptobacillus, HPV, HIV, and others.

Novel primer compositions useful for the amplification of nucleic acid and related methods are provided as well.

These and other advantages and aspects of the invention will be understood upon consideration of the following detailed description thereof.

BRIEF DESCRIPTION OF THE DRAWINGS

The drawings are not necessarily to scale, emphasis instead generally placed upon illustrating the principles of the invention.

FIG. 4 is another ethidium bromide-stained gel showing DNA amplification blocked by a PNA probe in accordance with methods of invention illustrated by FIG. 2;

DETAILED DESCRIPTION OF THE INVENTION

Figure 1:
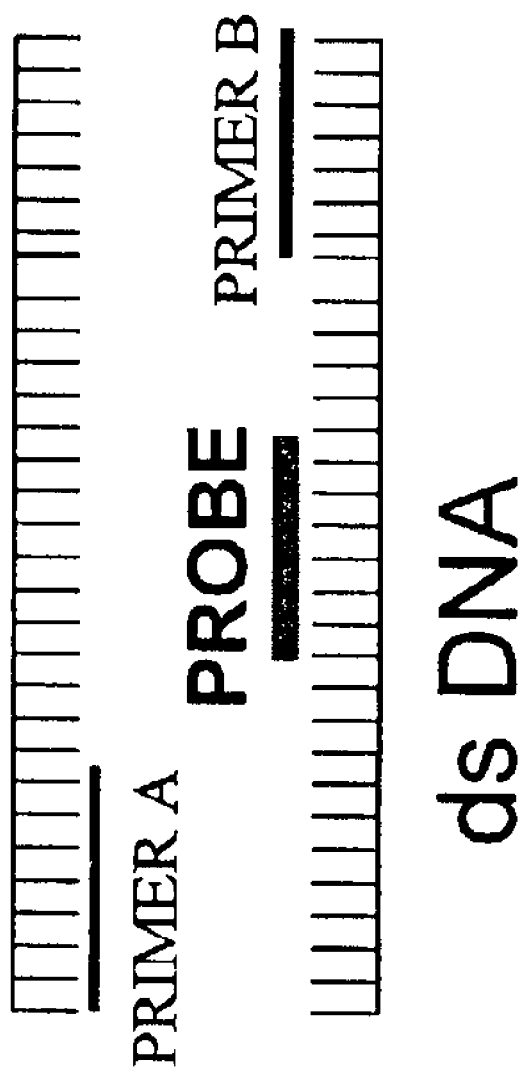
FIG. 1 provides a schematic illustration of certain methods of the invention.

In one aspect, methods of the present invention comprise screening patient samples for the presence of a high-risk HPV variant using at least one PNA probe. In a preferred embodiment, PNA probes that hybridize to portions of nucleic acids of multiple HPV types are used. Accordingly, the invention allows simultaneous detection of multiple strains or types of HPV.

Several PNA probes have been shown to cross-hybridize with nucleic acids from multiple HPV strains. Thus, in some instances, a single probe or a mixture of probes may be used to screen for the presence of multiple strains in a single sample. Also according to the invention, a PNA probe which hybridizes only to nucleic acid of a single HPV strain may be used to specifically identify and/or type that strain in a sample. Such highly specific probes can be used in series or in parallel by, for example, utilizing differentiable markers attached to the probes. A mixture of such highly specific probes or a mixture of such highly specific probes and cross-hybridizing probes may be used to identify multiple strains of HPV, preferably all the high-risk ones and only the high-risk ones.

Hybridization screening as described above also may be performed in a preservative solution to combine cytological screening of a patient sample (e.g., a PAP smear) with HPV screening. An exemplary preservative solution has a water-miscible alcohol in an amount sufficient to fix mammalian cells, an anti-clumping agent in an amount sufficient to prevent the cells from clumping in the solution, and a buffering agent maintaining the solution, with the cells, at a pH range between about 2 to about 7. A commercially available example is PreservCyt® solution from Cytyc Corporation (Boxborough, Mass.). The PreservCyt® solution is described in co-owned U.S. Pat. No. 5,256,571, incorporated herein by reference.

According to methods of the invention, PNA probes are designed to be substantially complementary to portions of nucleic acids of one or more HPV types. HPV DNA sequences can be found in numerous public databases, such as GENBANK. PNA probes for use in the invention were designed to hybridize to homologous regions of one or more HPV strains. In a preferred embodiment, homologies that are common among high-risk HPV strains but not common among low-risk HPV strains are selected to ensure the specificity of PNA probes to high-risk types of HPV DNA only.

A preferred region of homology is the HPV L1 consensus region. The L1 region has been known to encode for the major capsid protein of HPV and is retained whenever viral integration occurs in a cell. Other regions in the viral genome, e.g., the E6 open reading frame as known in the art, described in U.S. Pat. No. 5,888,724 to Silverstein et al. and incorporated herein by reference, can also be used to generate homologies.

DNA sequences of the L1 regions of various HPV types were downloaded from GENBANK. L1 regions of high-risk HPV types were then compared using Vector NTI software (Informax Inc., North Bethesda, Md.) to establish areas of homology. Thereafter, areas of homology that are common among known high-risk types of HPV but not common among low-risk types of HPV were selected. This was to ensure that any PNA probe so constructed would exhibit maximal specificity for the high-risk types of HPV but minimal or no specificity for the low-risk types of HPV. The selected sequences were then analyzed with the Vector NTI program to discard any sequence that would form significant secondary structure (e.g., hairpins).

The regions of homology were then used to generate PNA probes useful in screening assays. Examples of the probes generated include PNA Probes I–V:

```
5' ACT-GTT-GTT-GAT-ACT 3'    (SEQ ID NO: 1)
5' AGA-TAC-CAC-TCC-CA 3'     (SEQ ID NO: 2)
5' GAT-ACC-ACT-CGC-AG 3'     (SEQ ID NO: 3)
5' CCT-TAC-ACC-ACC-GC 3'     (SEQ ID NO: 4)
5' GAC-ACT-ACC-CGC-AG 3'.    (SEQ ID NO: 5)
```

Typically, the probes should be short enough to stay in solution, i.e., less than 18 or 19 bases. In constructing the probes, preferably for any stretch of 10 bases in a sequence, there is no more than 6 purines. Also, 4 to 5 purines in a row, especially 3 guanines in a row, preferably should be avoided. A preferred length of a PNA probe is 8 or more units. The present invention also contemplates the use of hybrids between PNA and other nucleic acids, such as DNA and RNA, as probes for detecting multiple strains of interest. PNA-DNA chimeras, which is known in the art and described in Uhlmann, E., Biol. Chem. 1998, 379 (8–9): 1045–52, the disclosure of which is incorporated herein by reference, can be useful in methods of the present invention.

Once the sequence of a PNA probe is finalized, a probe can be synthesized, purified and labeled according to methods known to those skilled in the art. For example, such methods are disclosed in PCT publication WO92/20702, U.S. Pat. No. 5,539,082 to Neilsen et al. and U.S. Pat. No. 5,731,416 to Garner, all incorporated herein by reference to the extent applicable. Such synthesis, labeling (e.g., with biotin) and purification of PNA probes can also be obtained from commercial vendors such as PerSeptive Biosystems Inc. (Framingham, Mass.).

"Molecular beacon" probes may also be employed in the methods of the present invention for direct visualization of hybridization between a probe and a target template. Molecular beacon probes are well known in the art and described in Tyagi et al., PCT application Nos. WO 95/13399, WO 97/39008, and U.S. Pat. No. 6,037,130 to Tyagi et al. all of which are incorporated herein by reference to the extent applicable. Molecular beacons are single-stranded nucleic acid probes that possess a stem-and-loop structure in which the loop portion of the molecule is a probe sequence complementary to the target nucleic acid sequence, such as an HPV sequence.

The stem of a molecular beacon probe is generated by the annealing of two complementary arm sequences, each located at either end of the probe sequence. The arm sequences are unrelated (i.e., not complementary) to the target sequence and each arm is labeled at its end. To one arm is attached a fluorescence moiety (i.e., at the 5' terminal phosphate) and to the other a non-fluorescent quenching molecule (i.e., at the 3' terminal hydroxyl group). In its nascent state, the molecular beacon emits no fluorescence. This is because the fluorescent-quencher pair is selected such that energy gained by the fluorophore is transferred to the quencher and is dissipated as heat, an occurrence that is referred to as fluorescence resonance energy transfer (FRET). At temperatures slightly above $T_m$, the stem portion of a molecular beacon unfolds and exposes the probe section of the molecule to target strands. Once exposed, the beacon and target hybridize.

Upon hybridization, a molecular beacon interacts with the target and undergoes a conformational change whereby the arm sequences of the beacon are forced apart such that the fluorophore and the quencher are physically distant from each other and their original positions. When the fluorophore is no longer in the proximity of the quenching molecule, FRET is no longer possible, and the fluorophore will then emit detectable light of appropriate wavelength when excited. When the PNA probe in accordance with the invention is constructed as a molecular beacon molecule, having a loop portion of PNA complementary to target nucleic acids, the hybridization between the probe and the target template can be detected using a fluorescence reader, either in "real-time" or "end-point" fashion. Examples of such fluorescence reader include the i-Cycler commercially available from Bio-Rad Laboratories (Hercules, Calif.) and the Roche Light Cycler commercially available from Hoffmann-La Roche Ltd. (Basel, Switzerland).

In one embodiment of the invention, a molecular beacon probe comprising a stem-and-loop structure is constructed where the loop portion is a PNA sequence complementary to the target DNA, for example, a particular HPV strain, to provide real time detection of the target DNA. The stem portions are not complementary to the target HPV sequence and provide FRET in the nascent state. The stem portions may be nucleotides other than PNA, such as DNA or RNA. Again, chimeric probes such as PNA-DNA chimeras, have been described in the art.

The PNA probes of the present invention are contemplated to be useful in any detection assay of HPV genetic materials. In one embodiment, sample DNA isolated from a cervical specimen previously suspended in PreservCyt solution is first and optionally amplified using PCR with a pair of consensus primers, MY09 and MY11:

```
MY09   5' CGTCCMARRGGAWACTGATC 3'    (SEQ ID NO: 6)
MY11   5' GCMCAGGGWCATAAYAATGG 3'    (SEQ ID NO: 7)
``` where M represents a mixture of adenine and cytosine
R represents a mixture of adenine and guanine
W represents a mixture of adenine and thymine
Y represents a mixture of cytosine and thymine
MY09 and MY11 each bind to different segments of HPV DNA's L1 region and amplify both DNA of high and low risks HPV strains. Amplification product is then contacted with biotin-labeled PNA probes specific for the DNA of high-risk HPV strains and allowed to hybridize. The solution containing hybridized PNA:DNA duplex is then applied to avidin-coated microtiter plates. After appropriate incubation and wash, a labeled antibody able to distinguish a PNA:DNA duplex from other nucleic acid complex is used for visualization of any hybridization. Such antibody is known in the art and described, e.g., in Hansen et al., J Immunol Methods, (1997), 203(2): 199–207, incorporated herein by reference. The antibody may be labeled with a detectable marker including but not limited to: a radioisotope, or a calorimetric marker (e.g. digoxigenin), a luminescent marker, a fluorescent marker or an enzyme (e.g. alkaline phosphatase). Such markers are known in the art.

Further, the primary antibody can in turn be recognized by a labeled secondary antibody for detection purpose.

In another embodiment of the invention, biotin-labeled DNA probes such as ALU probes are first used to hybrid-capture HPV DNA of all types onto an avidin-coated microtiter plate. After appropriate incubation and wash, PNA probes are added to the plate for hybridization. Detection of hybridization can be carried out using antibodies as described in the previous paragraph.

The present invention also includes kits that contain probes made in accordance with the invention or preservation solution or both, and may include other reagents needed for a detection assay. For example, a kit may include materials, instruments and devices for taking cervical samples, for storing the samples and for isolating and purifying genetic materials from the samples. An in vitro hybridization kit may include multiple probes, e.g., PNA probes made in accordance with the invention and ALU oligonucleotide probes, and other reagents needed for hybridization reactions. Any of these probes may be labeled, e.g., with biotin or a fluorophore. Kits made in accordance with the present invention may further include enzymes, primers (e.g., MY09/MY11), buffers and other reagents for a nucleotide-amplification reaction. An in situ hybridization kit may include enzymes, fixation solution, buffers and other reagents needed for slide preparation, signal amplification and other techniques employed in in situ hybridization. A kit may also include enzymes, antibodies, substrates and other reagents needed for labeling, detection and visualization of a target molecule. Such kits may also include probes and reagents needed for further HPV typing.

According to another aspect of the invention, methods and materials are provided for clinical assay of a biological sample to identify one or more selected nucleic acid variants by blocking amplification of non-selected variants. In a preferred embodiment, methods are used to detect one or more selected strains or variants of a disease organism, such as the DNA or RNA of a bacterium, yeast, other microbe, or a virus. The methods comprise amplifying a disease organism's nucleic acid using consensus primers capable of amplifying nucleic acids from several and preferably all strains or variants of the organism, while blocking amplification of nucleic acids from non-selected strain(s). The presence of amplification product indicates presence of the selected strain(s). No labeled probes are necessary. No probes that hybridize with sequences characteristic of the strain(s) of interest are necessary either. In a preferred embodiment, PCR is used to amplify the nucleic acid, and blocking-probes made of PNA are used.

In a preferred embodiment, a gynecological cell sample is obtained from a female subject to screen for strains of HPV that indicate high-risk of cervical cancer. Such a sample may be suspended, for example, in a PreservCyt® preservative solution. DNA from the sample is isolated and purified using kits and methods well known to one skilled in the art.

In one method embodying the invention, a pair of consensus primers, for example, MY09 and MY11, are selected as primers for a PCR reaction as illustrated in FIG. 1. Primers MY09 and MY11 (SEQ IDS NOS: 6 and 7) bind to portions of the HPV L1 consensus region. The L1 consensus region is retained whenever viral integration occurs in a cell. However, other regions in the HPV viral genome, such as the L2, E1, E6 and E7 open reading frames, are also useful as candidate region for amplification. For example, primers F1–F8 and R1–R6, shown below, amplify multiple HPV strains by amplifying a region in the E6 open reading frame:

Forward primers F1–F8:

(SEQ ID NO: 8)
5' TGT-CAA-AAA-CCG-TTG-TGT-CC 3';

(SEQ ID NO: 9)
5' TGT-CAA-AAA-CCG-TTG-TGT-CCA-AC 3';

(SEQ ID NO: 10)
5' TGT-CAA-AAA-CCG-TTG-TGT-CCA-GC 3';

(SEQ ID NO: 11)
5' TGC-CAG-AAA-CCA-TTG-AAC-CC 3';

(SEQ ID NO: 12)
5' TGT-CAA-AGA-CCA-CTC-GTG-CC 3';

(SEQ ID NO: 13)
5' TGT-CAA-AAA-CCG-TTG-TGT-CCT-GA 3';

(SEQ ID NO: 14)
5' TAT-GTG-ATT-TGT-TAA-TTA-GGT-G 3';

(SEQ ID NO: 15)
5' TGC-CAA-AAA-CCA-CTG-TGT-CC 3';

and Reverse Primers R1–R6:

(SEQ ID NO: 16)
5' GAG-CTG-TCG-CTT-AAT-TGC-TC 3';

(SEQ ID NO: 17)
5' TCT-GAG-TCT-CGT-AAT-TGC-TC 3';

(SEQ ID NO: 18)
5' TCT-GAC-TCG-CTT-TAT-TGC-TC 3';

(SEQ ID NO: 19)
5' TCT-GTG-CTG-TCA-ACT-TAC-TC 3';

(SEQ ID NO: 20)
5' CTG-AGC-TGT-CTA-ATT-GCT-CGT 3';

(SEQ ID NO: 21)
5' CTC-TGT-GTC-GCT-AAA-TTG-CTC-3';

Then, HPV-specific PNA blocking probes are constructed based upon published DNA sequences of various HPV strains (e.g., from GENBANK). In one embodiment, a blocking probe comprising PNA is designed to be substantially complementary to a portion in the L1 region, between the hybridization sites for primers MY09 and MY11 (SEQ ID NOS: 6 and 7), of low-risk HPV strains but not the high-risk HPV strains. In another embodiment, a blocking PNA probe substantially complementary to a portion of the E6 region of the low-risk but not the high risk HPV strains is designed. A subsequent PCR selectively amplifies only DNA from high-risk strains because exponential amplification of low-risk strains is blocked by the PNA probe. Segments between the hybridization sites of the primers up to the blocked region in the low-risk strains are replicated in a linear fashion rather than in an exponential way, resulting in no detectable amount of amplicon. In a preferred embodiment, the probe hybridizes to a region adjacent to a primer hybridization site, eliminating even truncated amplification product. Consequently, in methods of the invention, amplification product, i.e., a mass of nucleic acid above baseline level, is detectable through conventional DNA detection methods such as ethidium bromide staining, SYBR Green staining and other DNA staining. The presence of amplicon indicates the presence of high-risk strains in the sample. The size of the amplicon may be determined through simple gel electrophoresis or other methods and is used to further substantiate the presence of a high-risk strain. Conversely, the absence of amplification product indicates the lack of high-risk strains in the sample.

Multiple blocking probes can be constructed with specificity for nucleic acids from a different subset of the non-selected strains. When these multiple blocking probes are used as a "cocktail" in an amplification reaction, they together block amplification of all the non-selected strains. Therefore, in a particularly preferred embodiment, probes are constructed to block as many low-risk HPV strains as possible, such as type 11, 16, and 42–44, without blocking amplification of any high-risk strains. In a further preferred embodiment, at least one probe blocks amplification of all low-risk HPV strains through hybridization with low-risk HPV DNA within the region intended for amplification. Subsequent detection of amplification product, which is full-length between the primer set, indicates presence of high-risk strains in the sample while absence of amplification product indicates the lack of high-risk strains.

Figure 2:
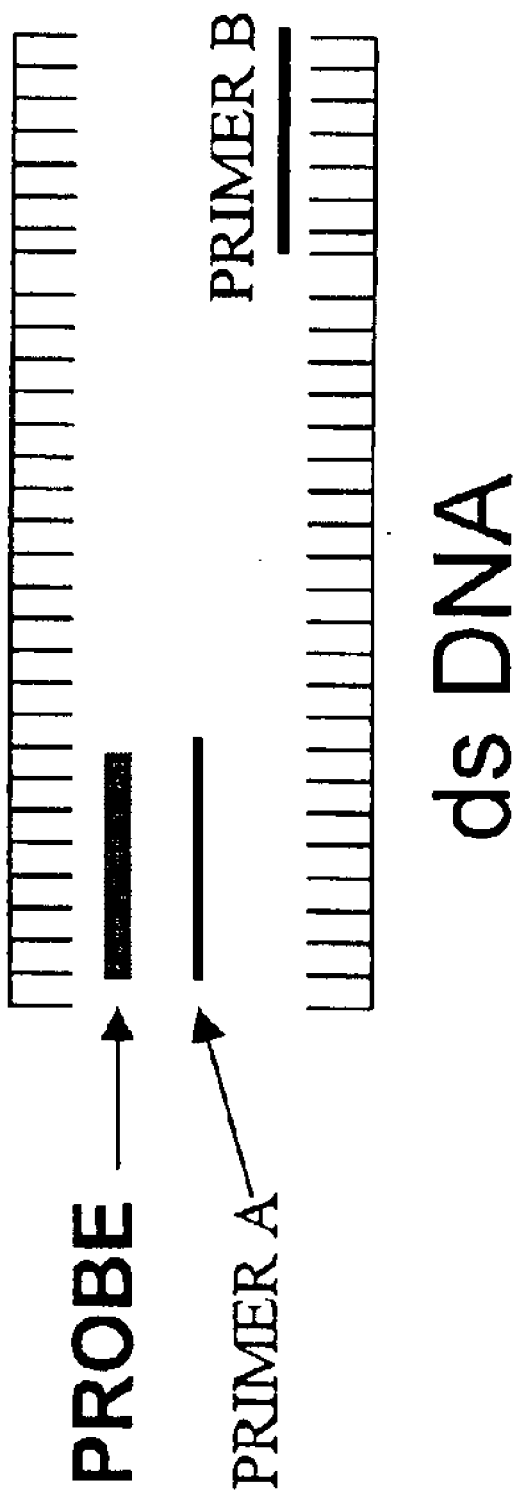
FIG. 2 provides a schematic illustration of more methods of the invention.

Referring to FIG. 2, a nucleic acid analog probe is constructed to hybridize partially or completely with a hybridization site of at least one of the primer pair. In a preferred embodiment, probes are made of PNA molecules or chimeras between PNA and another nucleotide such as DNA. Other types of probes that block amplification through sequence-specific hybridization may also be used. And the blocking probe, whether used in accordance with FIGS. 1 or 2, can be constructed to be a molecular beacon as described earlier. A molecular beacon blocking probe allows real-time detection of hybridization between the blocking probe and non-select strain's template.

Compared to DNA or RNA, PNA has a higher affinity for a substantially complementary nucleic acid template. Therefore, in a situation where a PNA probe competes with a DNA or RNA primer for part or all of a hybridization site, hybridization between the PNA probe and the nucleic acid template is favored. As a result, full-length amplification between the hybridization sites of the primer set will be inhibited. See U.S. Pat. No. 5,891,625 to Buchardt et al., the entirety disclosure of which is incorporated herein by reference.

Blocking probes used in embodiments illustrated by FIG. 2 may include one or multiple ("cocktail") blocking probes. Similar to what is described of the embodiments related to FIG. 1, detection of amplification product will indicate the presence of selected strains such as the high-risk strains of HPV.

Exemplary Method for Detecting HPV in A Cervical Scraping

A. Hybridization Assay Using PNA Probes

Methods of the invention are used to screen for the presence of HPV in cervical scrapings from several female patients. Scrapings are obtained by swabbing and placed in PreservCyt® solution at a concentration of about $2.0 \times 10^5$ epithelial cells per ml. The solution containing cells is mixed by vortex, and an aliquot of the sample is taken to make a "ThinPrep" slide for cytological analysis, as described in U.S. Pat. No. 5,143,627 to Lapidus et al., incorporated herein by reference. Specifically, the slide, where sample cells are uniformly transferred, is prepared using a ThinPrep Processor 2000® (Cytyc Corporation, Boxborough, Mass.).

A second aliquot of the sample solution is obtained for HPV analysis. The Buccal Swab DNA kit of Epicentre Technologies, Inc. (Madison, Wis.) is used for DNA extraction. The MY09/MY11 consensus primers (SEQ ID NOS: 6 and 7) (Research Genetics, Inc., Huntsville, Ala.) are used for PCR amplification.

For PCR, 100 ng (or 5 μl) of target DNA is mixed to a total volume of 50 μl with 10 mM Tris-HCl (pH 8.3), 5-mM KCl, 6 mM $MgCl_2$, 22 μM dNTP, 50 pmole of primer, 5 pmole β-globin primers PC04 and GH20, and 2.5 units Amplitaq DNA polymerase (Perkin Elmer Getus, P.W. Roche Molecular Systems, Inc., Branchburg, N.J.). Amplification of the β-globin gene is performed as a control to determine whether the sample is appropriate for HPV detection by PCR. PCR parameters are set at 35 cycles (95° C.-60 sec/55° C.-60 sec/72° C.-60° sec). Amplification products are detected by electrophoresis of one fifth volume of the reaction mix on a 1% agarose gel stained with ethidium bromide. Sample DNA is then extracted from the gel and in situ hybridization assay (as described below) is used to evaluate HPV status.

EXAMPLES

Example 1

Constructing and Testing of PNA Probes.

Biotin-labeled PNA probes complimentary to several high-risk types of HPV DNA were generated. The PNA probe sequences were based on areas of homology found in the L1 consensus region amplified by the MY09/MY11 (SEQ ID NOS: 6 and 7) degenerate primer set with information from the GENBANK database. Five PNA sequences, PNA Probes I–V, are identified (SEQ ID NOS: 1–5). Biotin-labeled PNA, 14 to 15 bases in length were synthesized to specification by PerSeptive BioSystems (Framingham, Mass.).

HPV-infected gynecological samples were stored in methanol-based PreservCyt solution (Cytyc Corporation, Boxborough, Mass.). DNA from these samples was isolated and purified using Epicenter's Buccal swab DNA extraction kit (Madison, Wiss.) with the following steps: a 2 ml aliquot of the PreservCyt cell suspension was pelleted by centrifugation at 8,000×g for 5 minutes. The supernatant was removed and the cell pellet resuspended in Epicenter's DNA extraction fluid and incubated at 60° C. for 30 minutes, 98° C. for 10 minutes, and chilled on ice for 5 minutes. The resulting extracted DNA was recovered from the supernatant solution after centrifugation at 8,000×g for 5 minutes.

The HPV DNA genotypes of residual PreservCyt cell suspensions were first determined by two separate methods. The first typing method was Polymerase Chain Reaction-Restriction Fragment Length Polymorphism (PCR-RFLP) analysis of HPV consensus primers (MY09/MY11, SEQ ID NOS: 6 and 7)-amplified L1 consensus region of HPV. PCR-RFLP was performed on specimen according to methods described by Lungo et al., *Mol. & Cell Probes*, v.10, p145–52, (1992), incorporated herein by reference to the extent applicable. Specifically, purified DNA was amplified in the presence of P-32 labeled CTP (and other appropriate NTPs) and then the amplicon was digested concurrently with Pst I, Rsa I, and Hae III. The restriction digest product was analyzed on polyacrylamide gels and HPV type size assigned based on HPV DNA standards. Detection was achieved by exposure to X-ray films.

In addition to PCR-RFLP, each positive specimen was typed by a second method using a commercially available hybridization HPV DNA typing kit (Alphagenics Diaco Biotech, Trieste, Italy) according to manufacture's instructions. Purified sample DNA was first amplified with DIG-labeled MY09/MY11 primer (SEQ ID NOS: 6 and 7). The amplicon was subsequently hybridized with biotin-labeled DNA probes specific to each type of HPV DNA. Hybridized duplexes were captured on avidin-coated microtiter plates and detected with enzyme-bound antibodies recognizing the DIG-labeled nucleic acid.

After a specific aliquot of sample DNA has been independently typed by these two methods, the DNA was amplified using MY09/MY11 primers to later be hybridized with constructed PNA probes. PCR-amplified DNA samples of various types of HPV were loaded on different columns of a 0.8% agarose gel and underwent electrophoresis. The size and presence of HPV L1 consensus amplicon were determined by Ethidium Bromide staining of agarose gel samples. The amplicons in the gel were depurinated, washed, and then denatured at room temperature. The gel was then neutralized (0.5 M Tris-HCl/1.5 M NaCl) at room temperature and the DNA transferred overnight from the agarose gel to a nylon membrane (Biodyne B membrane, PALL) through capillary diffusion. Successful transfer was determined by the absence of ethidium bromide bands on processed gel. The DNA was thereafter fixed to the membrane by heating for 30 minutes at 80° C. The membrane was re-hydrated in 2xSSC and pre-hybridized with blocking solution (100 mg/ml of salmon sperm DNA/5xSSC/5x Denhardt's solution/ 0.1% SDS) for 30 minutes at 68° C. Subsequently the membrane was hybridized with 20 nM of denatured biotin-labeled PNA probe overnight at 65° C.

After the membrane was removed from the hybridization solution and washed, presence of biotinylated PNA:DNA hybrids was established by chemiluminescent substrate assay which relies on phosphatase enzyme as the catalyst (Phototope Star detection kit from New England BioLabs). Final detection was obtained by exposure of the Southern blot to X-ray film (Kodak).

Table 1 shows the testing result for some of the PNA probes. A plus sign indicates that significant hybridization was observed between the PNA probe constructed according to a particular Sequence ID (row) and the particular type of HPV (column). A minus sign indicates the absence of such observation. A blank cell in the table indicates that hybridization reaction has not been carried out as specified yet.

probe including a molecular beacon has the following sequence where the underlined areas (five nucleotides on each side) are the stem portions of the beacon:

<u>GGCAC</u>ATCATCAAGAACCCGTAGAGAAACCCAGC<u>GTGCC</u> (SEQ ID NO: 22)

The above probe detects HPV type 16, which is a high-risk strain. Hybridization between the PNA probe and the target HPV can be detected, following conventional protocol, by using the i-Cycler commercially available from the Bio-Rad Laboratories.

Example 2

In Situ Hybridization

Step 1: Slide Preparation:

Cells fixed on ThinPrep slides are digested with proteolytic enzyme (i.e., 500 ul of 10 ug/ml proteinase K in 2xSSC, or with 500 ul of 0.2 N hydrochloric acid solution containing 0.05%–0.15% pepsin) at 37° C. for 30 minutes. The slides are then washed in 2xSSC for 2 minutes, ethanol dehydrated and air dried. Fifteen to 20 ul of the hybridization mixture containing 1 to 20 nM PNA probes are applied to each slide. Slides are then covered with glass coverslip and sealed.

Step 2: Hybridization

The PNA probes and target DNAs are co-denatured by placing the slides inside a thermocycler (MJ Research, Inc. Watertown, Mass.) and quickly bringing and maintaining the temperature of the thermocycler at 80° C. for three minutes. The interior temperature is afterwards rapidly dropped to

TABLE 1

| SEQ ID. | Type 6 | Type 11 | Type 16 | Type 18 | Type 31 | Type 33 | Type 35 | Type 39 | Type 45 | Type 51 | Type 52 | Type 53 | Type 56 | Type 58 | Type 68 |
|---|---|---|---|---|---|---|---|---|---|---|---|---|---|---|---|
| 1 | − | − | + | − | − | − | − | − | − | − | − | − | − | − | − |
| 2 | − | − | + | + | − | − | + | + | − | − | − | − | − | − | − |
| 3 | + | + | − | + | − | + | − | − | − | + | − | − | + | − | |
| 4 | − | − | − | − | − | − | + | − | − | − | − | − | − | − | |
| 5 | − | − | − | − | − | − | − | + | + | − | − | − | − | + | |

Detection of a target nucleic acid of HPV through hybridization with a labeled PNA probe prior to gel electrophoresis was also tested. PCR-Amplified DNA (1 ul) was mixed with 20 pM of biotinylated PNA probe I: 5' ACT-GTT-GTT-GAT-ACT 3' (SEQ ID NO: 1), in varying dilutions of the hybridization buffer. Amplicons, in the presence of PNA probes, were denatured for 10 minutes at 95° C., annealed rapidly and PNA:DNA duplexes were isolated on a 3% agarose gel. The presence of DNA may be determined by ethidium bromide staining. Thereafter, the DNA, without being denatured, was transferred onto a nylon membrane through capillary diffusion. Fixation to nylon was performed as described previously. DNA:PNA duplexes were detected and visualized using chemilumenscent substrate and X-ray films as described previously. In dilutions of hybridization buffer ranging from 1:1 to 1:1000, significant hybridization was observed between probe I and HPV DNA Type 16 from Caski cells, but none between the same probe and HPV DNA Type 18 from Hela cells. The pre-gel hybridization eliminates the need for in-gel denaturation and tedious hybridization and stringency washings, reduces hands-on time for detection assay, requires relatively small amount of PNA probes and works well on PCR products.

In another example, real time detection of hybridization between a target HPV and a labeled PNA or PNA-DNA chimeric probe may be achieved through the use of molecular beacon technology. An exemplary PNA-DNA chimeric 37° C., and the incubation is allowed to proceed from 15 minutes to 2 hours. Next, the slides are removed from the thermocycler, the coverslip are removed with forceps, and slides are washed for five minutes in 2xSSC at 75° C. Slides are then transferred to a Coplin jar containing 40 ml of phosphate buffered saline containing 0.05% Tween20 for 2 minutes.

Step 3: Post-Hybridization Wash and TSA Amplification

Amplification in the in situ assay can be performed by using commercial TSA-Indirect kit of NEN (Life Science Product at Boston, Mass.). Tyramide Signal Amplification systems are described by Sano et al. in "In situ hybridization with biotinylated tryamide amplification: Detection of human papillomavirus DNA in cervical neoplasia," *Modern Pathol* 1998; 11:19–23, incorporated herein by reference. Basic steps can be performed as follows: each slide from the previous step is incubated with 100 ul TNB Blocking Buffer (0.1 M Tris-HCl, pH 7.5, containing 0.15 M NaCl, and 0.5% blocking reagent) in a humid chamber for 30 minutes at room temperature. Plastic coverslips are used on the slides to reduce evaporation. Each slide receives 100 ul of strepavidin-horseradish peroxidase reagent (1:100 dilution in TNB Blocking Buffer), and is thereafter incubated for 30 minutes at room temperature while covered by cover slips. Next, slides are washed at room temperature with agitation in TNT Buffer (0.1 M Tris-HCl, pH 7.5 containing 0.15 M NaCl and 0.05% Tween), and to each slide 300 ul of biotinyl-tyramide is added. After incubation at room temperature for 3 to 10 minutes, the slides are once more washed in TNT buffer.

Step 4: Chromogenic Detection

About 100 ul of strepavidin-alkaline phosphatase (1:100 dilution in TNB Buffer) is added to each slide. Slides are incubated in a humid chamber while covered at room temperature for 5 to 10 minutes, and each slide is then washed in TNT Buffer. Hybridized PNA probes are detected by BCIP-NBT detection system according to manufacturer's instruction.

Step 5: Counterstain and Mounting

Slides are washed in distilled water, then counterstained with Eosin, coverslipped and mounted.

B. Use of PNA Probes in Selective Amplification of HPV DNA

A "ThinPrep" slide and sample DNA were prepared from suspended cervical scrapings specimens as described in Part A.

DNA sequences of the L1 consensus region of HPV strains available from GENBANK are used to generate PNA probes useful in the selective blocking of amplifications of the DNA templates extracted from the second aliquot. The resulting PNA probes included:

```
                               (SEQ ID NO: 23)
PNA Probe VI:    5' AGA-TAC-CAC-ACG-CAG 3'

(SEQ ID NO: 24)
PNA Probe VII;   5' TAG-ATA-CCA-CAC-GCA-GT 3'

(SEQ ID NO: 25)
PNA Probe VIII   5' AGA-TAC-CAC-TCC-CAG 3'
```

The PNA probes used are shown in SEQ ID NOS: 6–8. Typically, the probes should be short enough to stay in solution, i.e., less than 19 bases. In constructing the probes, for any stretch of 10 bases in a sequence, there are ideally fewer than about 7 purines.

PCR amplification reactions are then performed in the presence or absence of the probes with the MY-09/MY-11 primer set (SEQ ID NOS: 6 and 7) or modification thereof under the following conditions: initial denaturation step at 95° C. for 5 minutes, then 35 cycles of 95° C.-30 sec/54° C.-30 sec/72° C.-60 sec, with a final extension step of 2 minutes at 72° C. Other thermal cycling conditions may be also used for this application (e.g., initial denaturation step at 95° C. for 5 minutes, followed by 35 cycles 95° C.-30 sec/4° C.-60 sec/55° C.-30 sec/72–60 sec, with a final extension of 72° C. for 2 minutes. Additional alternatives may include a 25° C. PNA annealing temperature in place of the 4° C. step, as well as shortening the 4° C. step from 60 sec to 30 sec). The use of MY09 and MY11 primers to amplify and sequence the HPV L1 region is described in more detail in Bauer et al., JAMA 1991; 265:472–477, incorporated herein by reference.

PCR master mix may be in a final volume of 20 ul and consisted of 10 mM Tris-HCl pH 8.3, 25 mM KCl, 5 mM $MgCl_2$, 200 $\mu M$ of dNTP, 100 mnoles of each HPV L1 consensus primer, 1.0 units of Platinum Taq DNA polymerase (Gibco) and 100–750 ng of purified cellular DNA. DNA concentrations are determined by UV spectrophotometry by calculating the ratio between the readings at 260 nm and 280 nm. An $OD_{260}/OD_{280}$ provides an estimate of the purity of nucleic acids. The final PNA concentration is usually set at 10 $\mu M$. Amplification products can be detected by electrophoresis of three-fourths of the reaction mix on a 2% agarose gel stained with ethidium bromide.

Example 3

Testing PNA Probes Constructed According to Embodiments Illustrated by FIG. 1

PNA probes VI and VII (SEQ ID NOS: 23 and 24) were constructed in accordance with embodiments illustrated by FIG. 1. The sequences of both PNA probes VI and VII are substantially complementary to a homologous portion of low-risk HPV strains 6 and 11. Both probes bind to a portion between the binding sites for primer sets MY09/MY11.

Figure 3:
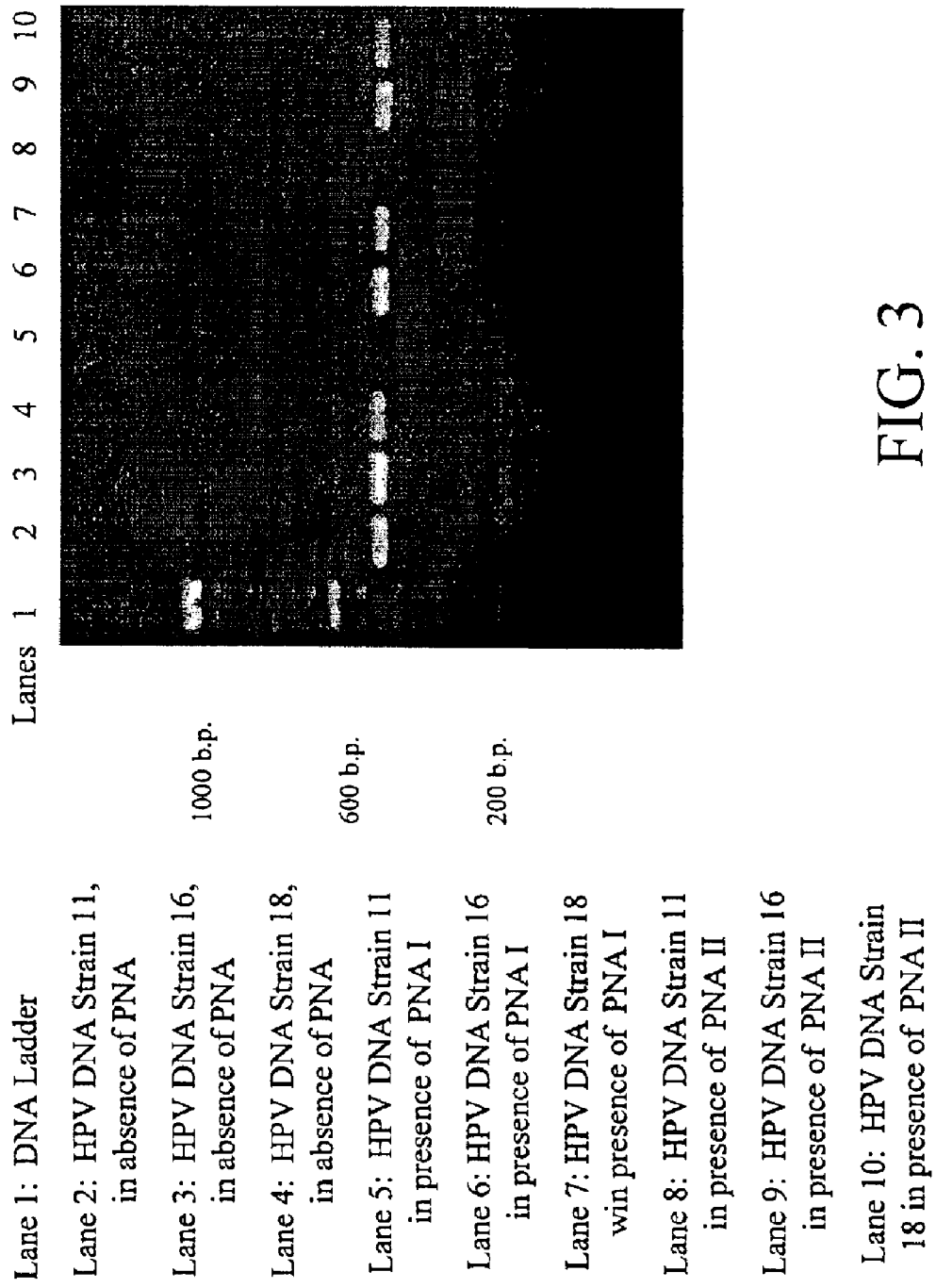
FIG. 3 is an ethidium bromide-stained gel showing selective amplification using PNA probes in accordance with methods of invention illustrated by FIG. 1.

DNA solutions of a known HPV strain were used to test the selective blocking capabilities of both probes in accordance with the present invention. As shown in FIG. 3, no PCR amplicon was observed in DNA samples of HPV strain 11 when either HPV probe VI and VII was used. PCR amplicon of the expected length was detected through ethidium bromide staining of the DNA of HPV strains 16 or 18 in the presence of either probe VI and VII. These results indicated that probes VI and VII, as they were designed for, were able to block amplification of HPV strain 11 and not 16 or 18.

Example 4

Testing PNA Probes Constructed According to Embodiments Illustrated by FIG. 2

A modified consensus primer MC01 was constructed with the following sequence: 5'-TGAGGAAGATACCACACGCAGT-3' (SEQ ID NO: 26). MC01 was used in conjunction with MY09 (SEQ ID NO: 6) and was capable of amplifying multiple HPV strains including strain 18. PNA probe VIII (SEQ ID NO: 25) was designed to comprise part of the primer MC01 with two base-pair modifications, which makes the probe 100% complementary to HPV strain 18's DNA and not to any other strains. PNA probe VIII was expected to compete with the modified consensus primer MC01 for binding to the DNA of HPV strain 18.

As shown in FIG. 4, DNA solutions of HPV strain 18 were used to test HPV probe VIII. No PCR amplicon was observed when various concentrations of HPV probe VIII were used. PCR amplicon of the expected length was detected through ethidium bromide staining of DNA sample in the absence of PNA probe VIII. These results indicated that probe III was able to compete and block amplification of HPV strain 18.

Example 5

Selective Amplification of HPV DNA in Regions Other Than L1

Primer pairs that amplify other regions of the HPV sequence, such as the E6/E7 regions, were used in PCR reactions to determine the presence of HPV in a sample. HPV probes useful for blocking the amplification of low-risk HPV strains were also used according to embodiments of the invention.

Sample DNA and cytological samples (e.g., "ThinPrep" slides) from female cervical scrapings were prepared as previously described, e.g., in Part A of this "Exemplary Method" section. The DNA samples were used for PCR as described below for diagnosing the presence of any HPV strains in the sample. Results from the PCR were compared to cytological observations for confirmation.

Primer pairs useful for replicating multiple or all of the high-risk HPV strains were constructed for use in PCR.

Exemplary primer pairs that are useful in methods embodying the invention include

```
Forward Primer F1:
5' TGT-CAA-AAA-CCG-TTG-TGT-CC 3';   (SEQ ID NO: 8)

and Reverse Primer R1:
5' GAG-CTG-TCG-CTT-AAT-TGC-TC 3'.   (SEQ ID NO: 16)
```

In addition, novel primers, both forward and reverse, were constructed using DNA sequences from the E6 region of HPV strains available from GENBANK. Homologies among different high-risk HPV strains were studied and primer sequences were designed based on these homologous areas. Examples include Forward Primers F2–F8:

```
                                   (F2, SEQ ID NO: 9)
  5' TGT-CAA-AAA-CCG-TTG-TGT-CCA-AC 3';

(F3, SEQ ID NO: 10)
  5' TGT-CAA-AAA-CCG-TTG-TGT-CCA-GC 3';

(F4, SEQ ID NO: 11)
  5' TGC-CAG-AAA-CCA-TTG-AAC-CC 3';

(F5, SEQ ID NO: 12)
  5' TGT-CAA-AGA-CCA-CTC-GTG-CC 3';

(F6, SEQ ID NO: 13)
  5' TGT-CAA-AAA-CCG-TTG-TGT-CCT-GA 3';

(F7, SEQ ID NO: 14)
  5' TAT-GTG-ATT-TGT-TAA-TTA-GGT-G 3';

(F8, SEQ ID NO: 15)
  5' TGC-CAA-AAA-CCA-CTG-TGT-CC 3';
``` and Reverse Primers R2–R6:

```
                                   (R2, SEQ ID NO: 17)
  5' TCT-GAG-TCT-CGT-AAT-TGC-TC 3';

(R3, SEQ ID NO: 18)
  5' TCT-GAC-TCG-CTT-TAT-TGC-TC 3';

(R4, SEQ ID NO: 19)
  5' TCT-GTG-CTG-TCA-ACT-TAC-TC 3';

(R5, SEQ ID NO: 20)
  5' CTG-AGC-TGT-CTA-ATT-GCT-CGT 3';

(R6, SEQ ID NO: 21)
  5' CTC-TGT-GTC-GCT-AAA-TTG-CTC-3';
```

Each of the above 14 primers was between 20–23 nucleotides. None of the 14 primers is identical to a contiguous stretch of DNA sequence in the following high risk strains: types 16, 18, 33, 35, 39, 51, 52, 56, 59, and 68. Methods embodying the invention can be practiced using any combination of the above primers, sequences complementary to them, or homologous sequences, such as those with 75% or 90% homology. Primer combination examples included (F1, R1) and (F1, R1, R6).

In one embodiment of the invention, multiple forward and reverse primers were used as a primer cocktail for PCR. For example, using F1, F5, F7, R1 and R5 in a cocktail, all the high risk strains studied (types 16, 18, 31, 33, 35, 39, 45, 51, 52, 56, 58, 59, and 68) were amplified. In another embodiment, all 14 primers (F1–F8 and R1–R6) were added as a cocktail for PCR.

An exemplary PCR protocol using the above primers is now described. Initial denaturation and Taq enzyme activation was performed at 94° C. for 5 min, then followed with 5 cycles of: denaturation at 94° C. for 30 sec., primer annealing at 55° C. for 1 min, and primer extension at 72° C. for 1 min. Then followed with 35 cycles of denaturation at 94° C. for 30 sec., primer annealing at 42° C. for 1 min., primer extension at 72° C. for 1 min. Final extension was carried out at 72° C. for 7 min. A typical DNA master mix was prepared in a final volume of 50 ul and consisted of 10 mM Tris-HCl pH 8.3, 50 mM KCl, 1.5 mM MgCl$_2$, 200 uM of mixed dNTPs, 2.5 units of Platinum Taq polymerase, 0.5 uM of each primer and 10 ul of purified DNA sample.

PNA probes useful for blocking the amplification of non-target nucleic acid, such as those of low-risk HPV stains but not high-risk HPV strains were constructed using DNA sequences of the E6 region of HPV strains. Specifically, one or more homologies found in the E6 region of low-risk strains but not the high-risk strains were used as the basis for designing such PNA probes. Examples of such probes included PNA Probes IX to XIII:

```
                                   (SEQ ID NO: 27)
  PNA Probe IX:    5' GTG-AAG-TAG-AAA 3'

(SEQ ID NO: 28)
  PNA Probe X      5' GTG-TGA-AGT-AGA 3'

(SEQ ID NO: 29)
  PNA Probe XI     5' CTG-TGT-GAA-GTAG 3'

(SEQ ID NO: 30)
  PNA Probe XII    5' GCT-GTG-TGA-AGT 3

(SEQ ID NO: 31)
  PNA Probe XIII   5' CGT-TGT-GTG-AAA-T 3'
```

As the following alignment shows, PNA Probes IX to XII are based on portions of the E6 region sequence of HPV 6 (portion underlined) and each probe overlaps with parts of the hybridization site in one of the primers, F1 (underlined):

```
F1:              TGTCAAAAACCGTTGTGTCC                   (SEQ ID NO: 8)

HPV 6 fragment:  TGTCACAAACCGCTGTGTGAAGTAGAAAAGGTAAAACAT (SEQ ID NO: 32)

PNA IX:                      GTGAAGTAGAAA              (SEQ ID NO: 27)

PNA X:                       GTGTGAAGTAGA              (SEQ ID NO: 28)

PNA XI:                      CTGTGTGAAGTAG             (SEQ ID NO: 29)

PNA XII:                     GCTGTGTGAAGT              (SEQ ID NO: 30)
```

PNA Probe XIII is based on a portion of the E6 region sequence of HPV 11 (see underlined portion) and also overlaps with part of the hybridization site in the F1 primer (underlined) as shown in the following alignment:

| | | |
|---|---|---|
| F1: | TGTCAAAAA<u>CCGTTGTGT</u>CC | (SEQ ID NO: 8) |
| HPV 11 fragment | TGTCACAAGC<u>CGTTGTGTGAAAT</u>AGAAAAACTAAAGCACATAT | (SEQ ID NO: 33) |
| PNA XIII: | CGTTGTGTGAAAT | (SEQ ID NO: 31) |

Referring to FIG. 2, in a method according to an embodiment of the invention, one of the PNA probes (IX to XIII) was added to a PCR that used F1 as one of the primers. The PNA probes, individually or together, were shown to block the amplification of low risk HPV strains such as 6, 11, and 44 while allowing the amplification of high-risk HPV strains such as 16, 18, 31, 33, 35, 39, 45, 51, and 53.

An example of the PCR protocol used in the above method with PNA probe follows. Initial denaturation and Taq enzyme activation was performed at 94° C. for 5 minutes followed with 40 cycles of: denaturation at 94° C. for 1 minutes, primer annealing at 55° C. for 1 minute, and primer extension at 72° C. for 1 minute. Then followed with final extension period carried out at 72° C. for 8 minutes. A typical DNA master mix was prepared with 20 mM Tris-HCl, 50 mM KCl, 1.5 mM MgCl$_2$, 200 uM of mixed dNTPs, 0.625 units of Platinum Taq polymerase, 0.1–2.5 uM of the primers and 60–80 uM PNA probe.

---

What is claimed is:

1. An essentially pure nucleic acid comprising a nucleic acid sequence selected from the group consisting of SEQ ID NO: 9, 10, 12, 13, 17–19 and 21.

2. The nucleic acid of claim 1, comprising SEQ ID NOS: 9.

3. The nucleic acid of claim 1, comprising SEQ ID NOS: 10.

4. The nucleic acid of claim 1, comprising SEQ ID NOS: 12.

5. The nucleic acid of claim 1, comprising SEQ ID NOS: 13.

6. The nucleic acid of claim 1, comprising SEQ ID NOS: 17.

7. The nucleic acid of claim 1, comprising SEQ ID NOS: 18.

8. The nucleic acid of claim 1, comprising SEQ ID NOS: 19.

9. The nucleic acid of claim 1, comprising SEQ ID NOS: 21.

10. A method for amplifying a target nucleic acid comprising selecting a primer selected from the group consisting of SEQ ID NOS: 9, 10, 12, 13 17–19 and 21, and amplifying said target nucleic acid.

11. The method of claim 10, wherein the method comprises a polymerase chain reaction.

12. The method of claim 10, further comprising selecting a primer selected from the group consisting of SEQ ID NOS: 8 and 16.

13. The method of claim 10, wherein a target nucleic acid of the amplification is a high risk strain of human papilloma virus.

14. The method of claim 10, further comprising selecting a probe comprising a nucleic acid analog to block full length amplification of a non-target nucleic acid.

15. The method of claim 13, wherein the non-target nucleic acid is of a low risk strain of human papilloma virus.

* * * * *